United States Patent [19]

Yokota et al.

[11] Patent Number: 4,918,211

[45] Date of Patent: Apr. 17, 1990

[54] SURFACE ACTIVE COMPOUNDS HAVING A POLYMERIZABLE MOIETY

[75] Inventors: Kinya Yokota, Shiga; Akinobu Ichihara, Kameoka; Hitoshi Shinike, Kyoto, all of Japan

[73] Assignee: Dai-Ichi Kogyo Seiyaku Co., Ltd., Kyoto, Japan

[21] Appl. No.: 119,460

[22] Filed: Nov. 10, 1987

[30] Foreign Application Priority Data

Dec. 12, 1986 [JP] Japan .................................. 61-297229
Dec. 12, 1986 [JP] Japan .................................. 61-297230
Dec. 12, 1986 [JP] Japan .................................. 61-297231

[51] Int. Cl.$^4$ ............................................ C07C 143/11
[52] U.S. Cl. ........................................ 558/31; 558/33; 558/34; 558/37; 558/51; 558/186; 558/187; 568/608; 568/616; 568/654
[58] Field of Search ................ 558/31, 51, 186, 187, 558/33, 34, 32, 37, 29; 560/193; 568/608, 616, 654

[56] References Cited

U.S. PATENT DOCUMENTS

| | | | |
|---|---|---|---|
| 2,573,769 | 11/1951 | Lambrech | 558/33 |
| 3,269,925 | 8/1966 | Rose | 558/186 |
| 3,551,479 | 12/1970 | Emmons | 560/193 |
| 3,565,939 | 2/1971 | Beiser | 558/33 |
| 3,619,123 | 11/1971 | Walz | 558/33 |
| 3,632,787 | 1/1972 | Wilbur | 524/831 |
| 3,666,843 | 5/1972 | Fearing | 558/186 |
| 3,723,578 | 3/1973 | Eiseman, Jr. et al. | 558/186 |
| 3,872,187 | 3/1975 | Fath | 558/186 |
| 3,875,202 | 4/1975 | Steckler | 558/31 |
| 4,231,781 | 11/1980 | Eiseman | 558/186 |
| 4,233,166 | 11/1980 | Allen | 558/33 |
| 4,814,514 | 3/1989 | Yokota et al. | 568/608 |

FOREIGN PATENT DOCUMENTS 0264867 4/1988 European Pat. Off. .

Primary Examiner—Jacqueline V. Howard
Assistant Examiner—Margaret B. Medley
Attorney, Agent, or Firm—Millen, White & Zelano

[57] ABSTRACT

Novel surfactants of the formula:

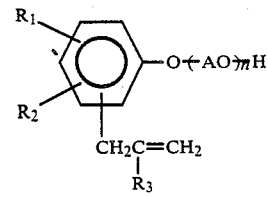

wherein $R_1$ is alkyl, alkenyl or aralkyl of 4–18 carbon atoms, $R_2$ is hydrogen or same as $R_1$, $R_3$ is hydrogen or methyl, A is alkylene of 2–4 carbon atoms, and n is 1–200. Sulfates, phosphates and sulfosuccinates thereof are also useful as anionic surfactants.

14 Claims, No Drawings

SURFACE ACTIVE COMPOUNDS HAVING A POLYMERIZABLE MOIETY

BACKGROUND OF THE INVENTION

This invention relates to novel surface active compounds having a polymerizable allyl or methally group which are particularly useful as an emulsifier in the emulsion or suspension polymerization of various monomers to produce an aqueous suspension of polymer particles.

A variety of surfactants having emulsifying, dispersing, detergent, wetting, foaming and other properties have been used in various products including textile materials, rubber and plastic products, pesticides, metals, paints, pigments, construction materials and the like while utilizing such properties. Recently, active efforts have been paid to obtain better acceptance of such products among end users by using a suitable surfactant. As a result of such activities, certain defects associated with the use of conventional surfactant have been revealed.

For instance, the use of certain surfactants is indispensable for the manufacture, stabilizing or workability of paints, printing inks, adhesives and the like. After these products have been used in painting, printing, bonding or other applications, no longer the presence of such surfactants is necessary but often adversely affects the water resistance, oil resistance or other properties of the resultant films or layers. As a countermeasure of these problems, various approaches have been studied including the reduction of the quantity of surfactant or the use of a surfactant having a large molecular weight. However, they are not compatible with the storage stability and/or workability of products to be imparted by the surfactant.

Surfactants are used in the emulsion- or suspension polymerization of monomers for the production of water-based polymer emulsions or suspensions. Examples of surfactants which have been used today for such application include anionic surfactants such as alkyl sulfates, alkylbenzenesulfonates, dialkylsulfosuccinates and polyoxyalkylene alkyl (or aryl) ether sulfates; and nonionic surfactants such as polyoxyalkylene alkyl (or aryl) ethers, polyoxyethylenepolyoxypropylene block copolymers and polyoxyethylenesorbitan fatty acid esters. These surfactants may be used either singly or in combination. However, polymer emulsions and films formed therefrom including these conventional surfactants are far from complete satisfaction in respect to emulsion stabilities and film properties. Thus, many problems still remain unsolved including the polymerization, mechanical, chemical, freeze and storage stabilities and the pigment dispersing property of resultant polymer emulsions incorporating conventional emulsifiers. When films are formed from these polymer emulsions, the water resistance and adhesion thereof are often impaired by the presence of unbound surfactants in the films. When these emulsions are destructed by means of, for example, salting out to recover polymer particles therefrom, a large amount of waste liquid containing the surfactant are necessarily formed as a by-product. For environmental reasons, this liquid must be subjected to expensive and complicated on-site water-treating processes before it can be disposed as effluent.

A number of patent documents discloses a novel type of surfactants which are polymerizable, degradable or otherwise reactive during or after use so as to be free from the foregoing defects. Examples of Japanese patent documents describing reactive anionic surfactants are listed as follows: Patent Application 46-12472, 46-34894, 49-46291, 56-29657, and Laid Open Publication 51-32085, 54-14431and 56-127697. Examples of Japanese patent documents describing reactive nonionic surfactants include Laid Open Applications 50-98484 and 56-28208.

Such reactive surfactants are mainly used in the emulsion polymerization of various monomers but they are not fully satisfactory in the practical application for such uses. One reason therefor is the fact that they are too expensive due to low yields or expensive starting materials. Another reason is that their properties such as emulsifying and dispersing capacities are less than those of conventional surfactants. Finally, despite the presence of a polymerizable moiety, they are not fully suited for such uses.

SUMMARY OF THE INVENTION

It is an object of this invention to provide new surfactant compounds having a polymerizable moiety which are free from the foregoing defects.

Other objects and advantages of this invention will become apparent to those skilled in the art upon further study of the specification and appended claims.

According to this invention, these objects have been achieved by providing compounds of the formula:

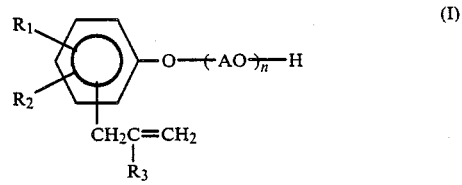

(I)

wherein $R_1$ is alkyl, alkeny or aralkyl of 4–18 carbon atoms, $R_2$ is hydrogen, or same as $R_1$, $R_3$ is hydrogen, or methyl, and A is alkylene of 2–4 carbon atoms, and n is 1–200.

The present invention also provides anionic surfactant compounds derived from compounds of the formula (I). They are sulfates, phosphates and sulfosuccinates of the formulas (II) through (VI), respectively:

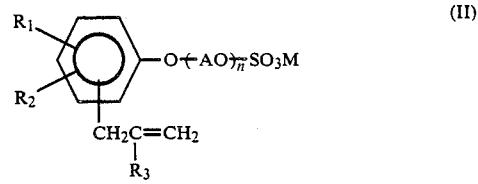

(II)

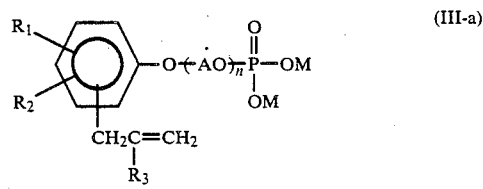

(III-a)

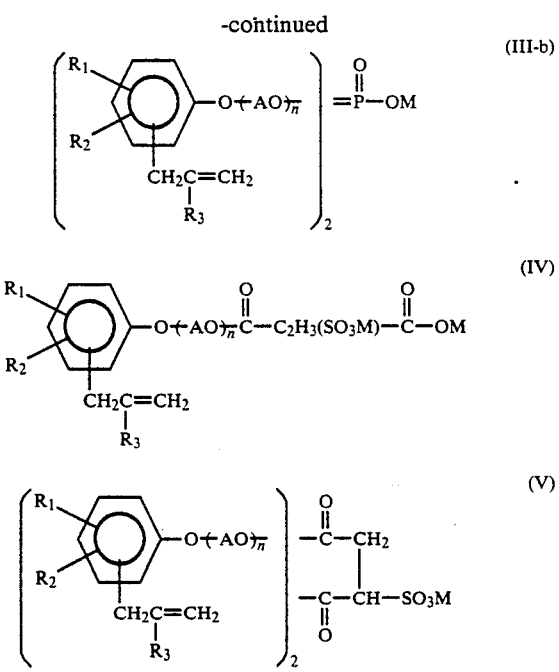

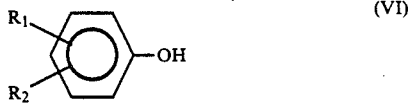

wherein M is hydrogen, alkali metal, NH4 or lower alkanolamine, and other symbols are as defined.

DETAILED DISCUSSION

The compounds of this invention of the above formula (I) may be prepared by reacting a phenol of the formula:

(VI)

first with allyl chloride or methallyl chloride, and then with an alkylene oxide of 2–4 carbon atoms.

The starting phenols may have as $R_1$ and $R_2$ upto two hydrocarbon substituents of an alkyl, alkenyl or aralkyl of 4–18 carbon atoms. Examples of such substituents include alkyls such as butyl, isobutyl, sec-butyl, pentyl, hexyl, heptyl, octyl, nonyl, decyl, undecyl, dodecyl, tridecyl, tetradecyl, pentadecyl, hexadecyl, heptadecyl and octadecyl; alkenyls corresponding to these alkyls; and aralkyls such as styryl, benzyl and cumyl. $R_1$ and $R_2$ may be same or different from each other.

Alkylation of the phenols of the formula (VI) with allyl chloride or methallyl chloride may be conveniently performed by any conventional alkylating technique in the presence of a catalyst such as an alkali metal carbonate.

The compounds (I) of this invention are produced by reacting the resultant allyl- or methallylphenols with 1–200, preferably 2–100 moles of alkylene oxide of 2–4 carbon atoms such as ethylene oxide, propylene oxide and butylene oxide.

The reaction may be carried out in the presence of a conventional basic or acidic catalyst. The oxyalkylene moieties included in the compounds (I) may be homopolymers, block or random copolymers of straight or branched alkylene oxides of 2–4 carbon atoms. These oxyalkylene moieties must, however, contain a sufficient number of oxyethylene units to render the moieties hydrophilic when they are copolymers containing alkylene oxides of 3 or 4 carbon atoms.

The nonionic surfactant compounds of the formula (I) may be converted to anionic surfactant compounds by chemically modifying the terminal hydroxyl group thereof.

One such approach includes the steps of reacting the compounds of the formula (I) with sulfuric acid or sulfamic acid and then optionally converting resulting free sulfate esters (when sulfuric acid is used) or ammonium salts (when sulfamic acid is used) into corresponding alkali metal or alkanolamine salts such as monoethanolamine by conventional procedures whereby sulfate esters of the formula (II) are obtained.

Another approach includes the steps of reacting the compounds of formula (I) with phosphorus pentoxide or phosphorus oxychloride and then optionally converting resulting free phosphate esters into corresponding salts with alkali metal, ammonium or alkanolamine whereby mixtures of monoesters of the formula (III-a) and di-esters of the formula (III-b) are obtained. These mixtures may be used as an anionic surfactant without isolating into their constituents.

A further approach includes the steps of reacting the compounds of the formula (I) with maleic anhydride, reacting resultant maleate esters with an alkali metal bisulfite and then optionally converting resulting alkali metal sulfosuccinates into corresponding free acids or ammonium or alkanolamine salts. When at least one mole of maleic anhydride is used relative one mole of the compounds of the formula (I) in the above reaction, mixtures of half ester isomers having a sulfo group $SO_3M$ attached to either alpha or beta position relative to the terminal carboxyl group in the formula (IV) are obtained. These mixtures may also be used as an anionic surfactant without isolation. Conversely, at least two moles of the compounds of the formula (I) are reacted with one mole of maleic anhydride, di-esters of the formula (V) are obtained.

The new surfactant compounds of this invention can meet a user's demand for a reactive surfactant which no longer functions as a surfactant immediately after it has played a desired role in the manufacture, storage or processing of various products such as paints, printing inks and adhesives. These compounds may be rendered inactive after use by incorporating a suitable polymerization initiator to the formulations containing the same prior to coating, printing, bonding or other application steps and/or by curing the compounds with heat or UV ray.

The surfactants of this invention are particularly useful as an emulsifier in the emulsion or dispersion polymerization of ethylenically unsaturated monomers. Examples of monomers include acrylic monomers such as acrylic acid, methyl acrylate, butyl acrylate, 2-ethylhexyl acrylate, methyl methacrylate, acrylonitrile, acrylamide and 2-hydroxyethyl acrylate; aromatic monomers such as styrene and divinylbenzene; vinyl esters such as vinyl acetate; halogen-containing monomers such as vinyl chloride and vinylidene chloride; conjugated diene monomers such as butadiene, isoprene and chloroprene; ethylene, maleic anhydride and methyl maleate.

Any known initiator such as hydrogen peroxide, potassium persulfate, azobisisobutyronitrile and benzoyl peroxide may be used in the emulsion polymerization in combination with a known polymerization promoter such as sodium bisulfite and ammonium ferrous sulfate.

The surfactants of this invention may be used in an amount of 0.1 to 20%, preferably 0.5 to 10.0% by weight of the total monomers singly or in combination with a conventional emulsifiers or protective colloid.

The resulting polymer emulsions or dispersions may be applied on woods, metals, paper, textiles or concrete structures as an adhesive, coating agent or reinforcing agent.

The new surfactant compounds of this invention may find uses not only as an emulsifier or dispersant of various materials such as monomers in the emulsion or suspension polymerization, waxes, dyes, pigments and pesticides, but also as post-treating agents for textile materials and antistatic agents for plastic products. By the use of the surfactants of this invention, defects of conventional surfactants remaining after use may be alleviated.

The invention is further illustrated by the following examples, in which all parts and percentages are by weight unless otherwise specified.

EXAMPLE 1

A reactor having stirring means, thermometer and reflux condenser was charged with 220 g (1.0 mol) of nonylphenol and 5 g of potassium carbonate as a catalyst. 84 g (1.1 mol) of allyl chloride was added dropwise. The mixture was stirred at 40° C. for 2 hours and then at 220° C. for 3 hours. The reaction product was distilled in vacuo to give 209 g (80% of theory) of allyl-nonylphenol.

This product was transferred to an autoclave and reacted with 30 moles per mole of the phenol of ethylene oxide in the presence of potassium hydroxide catalyst at 130° C. at a pressure of 1.5 kg/cm². This product is hereinafter referred to as surfactant I-1.

Analogously to surfactant I-1, the following allyl-or methallylphenol/alkylene oxide adducts of the formula (I) were prepared.

| No. | $R_1$ | $R_2$ | $R_3$ | $(AO)_n$ |
|---|---|---|---|---|
| I-1 | Nonyl | H | H | EO 30 |
| I-2 | Octyl | " | " | EO 10 |
| I-3 | " | " | " | EO 85 |
| I-4 | " | " | " | EO 50, PO 5 (block) |
| I-5 | " | " | " | EO 20, PO 3, BO 2 (random) |
| I-6 | Di-sec-butyl | " | " | EO 15 |
| I-7 | Di-nonyl | " | " | EO 40 |
| I-8 | Di-styryl | " | " | EO 100 |
| I-9 | Nonyl | H | $CH_3$ | EO 30 |
| I-10 | Octyl | " | " | EO 10 |
| I-11 | " | " | " | EO 85 |
| I-12 | " | " | " | EO 50, PO 5 (block) |
| I-13 | " | " | " | EO 20, PO 3, BO 2 (random) |
| I-14 | Di-sec-butyl | " | " | EO 15 |
| I-15 | Di-nonyl | " | $CH_3$ | EO 40 |
| I-16 | Di-styryl | " | " | EO 100 |

EO = Ethylene oxide, PO = Propylene oxide, BO = Butylene oxide

EXAMPLE 2

A reactor having a stirrer and a thermometer was charged with 350 g (0.5 mol) of surfactant I-1 obtained in Example 1 and 58.2 g (0.6 mol) of sulfamic acid. The mixture was heated at 120° C. for 3 hours with stirring. After unreacted sulfamic acid was filtered off, the ammonium salt of sulfate of surfactant I-1 was obtained. This product is referred to as surfactant II-1.

Analogously to surfactant II-1, the following sulfate esters of the formula (II) were produced.

| No. | $R_1$ | $R_2$ | $R_3$ | $(AO)_n$ | M |
|---|---|---|---|---|---|
| II-1 | Nonyl | H | H | EO 10 | $NH_4$ |
| II-2 | Octyl | " | " | EO 4 | " |
| II-3 | " | " | " | EO 85 | " |
| II-4 | " | " | " | EO 10, PO 5 (block) | " |
| II-5 | " | " | " | EO 20, PO 20, BO 2 (random) | " |
| II-6 | Di-sec-butyl | " | " | EO 35 | K |
| II-7 | Di-nonyl | " | " | EO 20 | Triethanolamine |
| II-8 | Di-styryl | " | " | EO 11 | $NH_4$ |
| II-9 | Nonyl | H | $CH_3$ | EO 10 | $NH_4$ |
| II-10 | Octyl | " | " | EO 4 | " |
| II-11 | " | " | " | EO 85 | " |
| II-12 | " | " | " | EO 10, PO 5 (block) | " |
| II-13 | " | " | " | EO 20, PO 20, BO 2 (random) | " |
| II-14 | Di-sec-butyl | " | " | EO 35 | K |
| II-15 | Di-nonyl | " | " | EO 20 | Triethanolamine |
| II-16 | Di-styryl | " | " | EO 11 | $NH_4$ |

EXAMPLE 3

A reactor having a stirrer and a thermometer was charged with 350 g (0.5 mol) of surfactant I-1 obtained in Example 1 and 22.7 g (0.16 mol) of phosphorus pentoxide. The mixture was heated at 80° C. for 5 hours with stirring. A mixture of mono- and di-phosphate esters in 50:50 molar ratio was obtained and referred to as surfactant III-1.

Similarly, the following mixtures of phosphate esters of the formulas III-a and III-b were prepared.

| No. | $R_1$ | $R_2$ | $R_3$ | $(AO)_n$ | M | Mono:Di (mole) |
|---|---|---|---|---|---|---|
| III-1 | Nonyl | H | H | EO 10 | H | 50:50 |
| III-2 | Octyl | " | " | EO 4 | H | 55:45 |
| III-3 | " | " | " | EO 85 | H | 70:30 |
| III-4 | Octyl | H | H | EO 10, PO 5 (block) | H | 60:40 |
| III-5 | " | " | " | EO 20, PO 3, BO 2 (random) | H | 50:50 |
| III-6 | Di-sec-butyl | " | " | EO 35 | K | 64:36 |
| III-7 | Di-nonyl | " | " | EO 20 | Triethanolamine | 95:5 |
| III-8 | Di-styryl | " | " | EO 11 | $NH_4$ | 50:50 |
| III-9 | Nonyl | H | $CH_3$ | EO 10 | H | 50:50 |
| III-10 | Octyl | " | " | EO 4 | H | 60:40 |
| III-11 | " | " | " | EO 85 | H | 65:35 |
| III-12 | " | " | " | EO 10, PO 5 | H | 55:45 |

-continued

| No. | $R_1$ | $R_2$ | $R_3$ | $(AO)_{\overline{n}}$ | M | Mono:Di (mole) |
|---|---|---|---|---|---|---|
| III-13 | " | " | " | (block) EO 20, PO 3, BO 2 (random) | H | 55:45 |
| III-14 | Di-sec-butyl | " | " | EO 35 | K | 60:40 |
| III-15 | Di-nonyl | " | " | EO 20 | Triethanol-amine | 80:20 |
| III-16 | Di-styryl | " | " | EO 11 | $NH_4$ | 55:45 |

EXAMPLE 4

A reactor having a stirrer, thermometer and condenser was charged with 350 g (0.5 mol) of surfactant I-1 obtained in Example 1 and 49 g (0.5 mol) of maleic anhydride. The mixture was heated at 80° C. for 3 hours with stirring to produce a maleic acid half ester. This product was diluted with 1330 g of water and then neutralized with 41.7 g of 48% sodium hydroxide (0.5 mol). Then 57.2 g (0.55 mol) of sodium bisulfite was added and the mixture allowed to react at 80° C. for 3 hours. Sodium salt of mono-sulfosuccinate ester of surfactant I-1 was obtained and referred to as surfactant IV-1.

Similarly, the following mono-sulfosuccinate esters of the formula (IV) were produced.

| No. | $R_1$ | $R_2$ | $R_3$ | $(AO)_{\overline{n}}$ | M |
|---|---|---|---|---|---|
| IV-1 | Nonyl | H | H | EO 10 | Na |
| IV-2 | Octyl | " | " | EO 4 | " |
| IV-3 | " | " | " | EO 85 | " |
| IV-4 | " | " | " | EO 10, PO 5 (block) | $NH_4$ |
| IV-5 | " | " | " | EO 20, PO 3, BO 2 (random) | " |
| IV-6 | Di-sec-butyl | " | " | EO 35 | Na |
| IV-7 | Di-nonyl | " | " | EO 20 | " |
| IV-8 | Di-styryl | " | " | EO 11 | " |

EXAMPLE 5

A reactor having a stirrer, thermometer and condenser was charged with 350 g (0.5 mol) of surfactant I-1 obtained in Example 1 and 24.5 g (0.25 mol) of maleic anhydride. The mixture was heated at 160° C. with stirring for 8 hours while removing condensed water. After cooling to 40° C., the reaction product was reacted with 26 g (0.25 mol) of sodium bisulfite in 60 g of water and 60 g of isopropyl alcohol at 80° C. for 5 hours. Sodium salt of di-sulfosuccinate ester of surfactant I-1 was obtained and referred to as surfactant V-1.

Similarly, the following di-sulfosuccinate esters of the formula (V) were prepared.

| No. | $R_1$ | $R_2$ | $R_3$ | $(AO)_{\overline{n}}$ | M |
|---|---|---|---|---|---|
| V-1 | Nonyl | H | H | EO 10 | Na |
| V-2 | Octyl | " | " | EO 4 | " |
| V-3 | " | " | " | EO 85 | " |
| V-4 | " | " | " | EO 10, PO 5 (block) | " |
| V-5 | " | " | " | EO 20, PO 3, BO 2 (random) | $NH_4$ |
| V-6 | Di-sec-butyl | " | " | EO 35 | " |
| V-7 | Di-nonyl | " | " | EO 20 | " |
| V-8 | Di-styryl | " | " | EO 11 | " |

EXAMPLE 6

The values of surface tension of the surfactants of this invention in a 0.1% aqueous solution were measured according to Traube's method and are shown in Table 1. Also shown, for comparative purposes, are the measured values for conventional surfactants of analogous structure.

TABLE 1

| Surfactant No. | Surface tension at 0.1% at 25° C. (dyne/cm) |
|---|---|
| II-1 | 42.0 |
| II-2 | 28.0 |
| II-3 | 51.0 |
| II-4 | 34.0 |
| II-5 | 43.0 |
| II-6 | 56.0 |
| II-7 | 32.0 |
| II-8 | 34.0 |
| II-9 | 41.0 |
| II-10 | 29.0 |
| II-11 | 50.0 |
| II-12 | 35.0 |
| II-13 | 42.0 |
| II-14 | 57.0 |
| II-15 | 31.0 |
| II-16 | 35.0 |
| III-1 | 41.0 |
| III-2 | 36.0 |
| III-3 | 44.0 |
| III-4 | 36.0 |
| III-5 | 42.0 |
| III-6 | 40.0 |
| III-7 | 32.0 |
| III-8 | 39.0 |
| III-9 | 39.0 |
| III-10 | 34.0 |
| III-11 | 42.0 |
| III-12 | 34.0 |
| III-13 | 40.0 |
| III-14 | 38.0 |
| III-15 | 30.0 |
| III-16 | 37.0 |
| IV-1 | 36.0 |
| IV-2 | 32.0 |
| IV-3 | 48.0 |
| IV-4 | 31.0 |
| IV-5 | 45.0 |
| IV-6 | 57.0 |
| IV-7 | 37.0 |
| IV-8 | 43.0 |
| V-1 | 37.0 |
| V-2 | 29.0 |
| V-3 | 46.0 |
| V-4 | 42.0 |
| V-5 | 40.0 |
| V-6 | 50.0 |
| V-7 | 36.0 |
| V-8 | 45.0 |

| No. | Controls | Surface Tension at 0.1% at 25° C. (dyne/cm) |
|---|---|---|
| C-1 | Sodium dodecylbenzenesulfonate | 36.0 |
| C-2 | Sodium lauryl sulfate | 45.0 |
| C-3 | Nonylphenol/EO 8 adduct sulfate $NH_4$ salt | 40.0 |
| C-4 | Nonylphenol/EO 8 adduct phosphate (mono:di = 58:42) | 38.0 |
| C-5 | Sodium dioctylsulfosuccinate | 33.0 |

EXAMPLE 7

The dispersing and emulsifying capacities of compounds of this invention were measured using carbon black and kerosin, respectively, and are shown in Table 2. Also indicated, for comparison purposes, are those of conventional surfactants of analogous structure.

The test methods used in these experiments are as follows:

Dispersing Capacity

Into a 100 ml measuring cylinder were placed 1 g of the surfactant of this invention and 10 g of carbon black. Water was added until a total volume of 100 ml was reached. The mixture was shaken 100 times for 1 minutes and then allowed to stand for 1 hour at 25° C. 30 ml of the dispersion was withdrawn from the cylinder and filtered through a glass filter. The residue on the filter was dried at 105° C. and weighed. The dispersing capacity was calculated by the following equation.

$$\text{Dispersing Capacity (\%)} = \frac{\text{Weight of Residue (g)}}{3 \text{ (g)}} \times 100$$

Emulsifying Capacity

Into a 20 ml measuring cylinder were placed 5 ml of 0.5% aqueous solution of the surfactant of this invention and 5 ml of kerosine. The mixture was shaken 100 times for 1 minutes and allowed to stand for 1 hour at 25° C. The volume of emulsified layer was measured. The emulsifying capacity was calculated by the following equation:

$$\text{Emulsifying Capacity (\%)} = \frac{\text{Emulsified Layer (ml)}}{10 \text{ (ml)}} \times 100$$

TABLE 2

| Surfactant No. | Dispersing Capacity (%) | Emulsifying Capacity (%) |
|---|---|---|
| II-1 | 60 | 70 |
| II-2 | 80 | 55 |
| II-9 | 70 | 75 |
| II-10 | 75 | 60 |
| III-1 | 80 | 75 |
| III-2 | 70 | 60 |
| III-9 | 85 | 70 |
| III-10 | 75 | 65 |
| IV-1 | 85 | 60 |
| IV-2 | 70 | 50 |
| V-1 | 70 | 55 |
| V-5 | 65 | 65 |
| Control C-1 | 70 | 55 |
| Control C-2 | 60 | 40 |
| Control C-3 | 80 | 60 |
| Control C-4 | 85 | 70 |
| Control C-5 | 20 | 50 |

EXAMPLE 8

5 g of the surfactant of this invention and 30 g of polyvinyl alcohol (saponification degree of 80 mole %, average viscosity polymerization degree of 1700) were dissolved in 300 g of water with stirring under warm. 240 g of vinyl acetate monomer was added dropwise and emulsion polymerized in the presence of 1 g of ammonium persulfate by the known method to prepare a polymer emulsion. To this emulsion was added 30 g of dioctyl phthalate.

The values of adhesion strength were measured and are shown in Table 3.

TABLE 3

| Surfactant | Normal Adhesion[1] Strength (kg/cm$^2$) | Water Resistance[2] Adhesion Strength (kg/cm$^2$) |
|---|---|---|
| II-1 | 185 | 120 |
| II-3 | 190 | 140 |
| II-8 | 180 | 100 |
| II-9 | 190 | 120 |
| II-11 | 170 | 110 |
| II-16 | 175 | 90 |
| III-1 | 195 | 110 |
| III-3 | 170 | 98 |
| III-8 | 190 | 140 |
| III-9 | 185 | 100 |
| III-11 | 160 | 90 |
| III-16 | 180 | 120 |
| IV-1 | 205 | 130 |
| IV-3 | 170 | 90 |
| IV-8 | 190 | 120 |
| V-1 | 180 | 130 |
| V-3 | 205 | 140 |
| V-8 | 175 | 95 |
| Control C-1 | 92 | 10 |
| Control C-3 | 86 | 20 |
| Nonylphenol/EO 10 adduct phosphate (mono:di = 80:20) | 78 | 5 |
| Lauryl alcohol/EO 20 adduct | 120 | 35 |

[1]Compression/shear adhesion strength of birch/birch test piece measured by the method according to JIS-K6804.
[2]The same measurement as above after soaking in water for 3 hours at 30° C.

EXAMPLE 9

A piece of polypropylene nonwoven fabric (2.5 cm × 10 cm) was soack in 1% aqueous solution of the surfactant of this invention for 1 minute and air dried at 120° C. The treated fabric was suspended in a 100 ml beaker containing 50 ml of water so that only 1 cm length of the distal end was submerged in water. After 5 minutes, the height of water-penetrated area above the liquid level was determined.

The above test was repeated for the same fabric after treating with the surfactant, drying and rinsing with tap water for 1 minutes. The results before and after the rinsing are shown in Table 4.

TABLE 4

| Surfactant No. | Before Rinsing (mm) | After Rinsing (mm) |
|---|---|---|
| II-4 | 15 | 14 |
| II-6 | 12 | 10 |
| II-12 | 14 | 12 |
| II-14 | 13 | 10 |
| III-4 | 16 | 13 |
| III-6 | 14 | 14 |
| III-12 | 17 | 14 |
| III-14 | 13 | 11 |
| IV-4 | 16 | 13 |
| IV-6 | 13 | 11 |
| V-4 | 17 | 16 |
| V-6 | 23 | 20 |
| Control C-1 | 18 | 1 |
| Octylphenol/EO 10 adduct sulfate Na | 14 | 0 |
| Octylphenol/EO 10 adduct phosphate (mono:di = 65:35) | 15 | 2 |

EXAMPLE 10

A solution of 10 parts of the surfactant of this invention in 290 parts of water was warmed to a temperature of 70° C. To this solution were added 20 parts of ethyl acrylate or vinyl acetate monomer and 0.1 parts of ammonium persulfate with stirring. 10 minutes after the initiation of polymerization reaction, additional 180 parts of the monomer were added dropwise over 3 hours with stirring. Then the mixture was stirred for additional one hour at 70° C. and allowed to cool.

The resulting polymer emulsion was applied on a glass plate, dried at room temperature for 24 hours and cured at 110° C. for 3 minutes to make a film. The polymer emulsion and the film made therefrom were tested for stabilities and water resistances. The results are shown in Table 5.

EXAMPLE 11

A solution of 5 parts of a combination of surfactants listed in the Table 7 below in 295 parts of water was warmed to 80° C. To this solution were added 0.3 parts of ammonium persulfate and 20 parts of a 7:3 monomer mixture of n-butyl acrylate and styrene with stirring. 10 minutes after the initiation of the polymerization reaction, additional 180 parts of the monomer mixture were added dropwise over 3 hours with stirring. Then the mixture was stirred for additional 1 hour at 80° C. and allowed to cool.

The resulting polymer emulsion and the films prepared therefrom were tested for stabilities and water resistances as in Example 10. The results are shown in Table 6.

TABLE 5

| Surfactant | Monomer | Emulsion Stability Polymerization[1] | Mechanical[2] | Polymer Film Water Resistance[3] Dried at R. T. | Dried at R. T. and cured at 110° C. |
|---|---|---|---|---|---|
| I-1 | Ethyl acrylate | Very good | Very good | Good | Very good |
| I-3 | " | Good | Good | " | " |
| I-9 | " | Very good | " | Very good | " |
| I-11 | " | Good | Very good | Good | " |
| II-1 | " | Very good | " | Very good | " |
| II-3 | " | " | " | Good | " |
| III-1 | " | " | " | " | " |
| III-3 | " | Good | Good | " | " |
| IV-1 | " | " | Very good | Very good | " |
| IV-3 | " | Very good | " | Good | " |
| V-1 | " | Good | Good | " | " |
| V-3 | " | " | Very good | " | " |
| Nonylphenol/EO 3 adduct | " | Very good | Fair | " | Good |
| Na Dodecylbenzene sulfonate | " | Good | Bad | Bad | Fair |
| I-1 | Vinyl Acetate | Good | Very good | Good | Very good |
| I-8 | " | Very good | " | " | " |
| I-9 | " | " | " | " | " |
| II-1 | " | " | " | Fair | Good |
| III-1 | " | Good | " | Good | Very good |
| IV-1 | " | " | " | " | " |
| V-1 | " | " | " | " | " |
| Nonylphenol/EO 20 adduct | " | " | Good | Bad | Fair |

[1]After polymerization, the polymer emulsion was filtered through a 150 mesh stainless steel screen. Agglomerates retained on the screen were thoroughly washed with water and weighed. Percents of the agglomerates relative to the charged quantity of the monomer was calculated.
Very good: <0.5%
Good: 0.5-2%
Fair: 2-5%
Bad: >5%
[2]The emulsion was centrifuged in a Marlon type mechanical stability tester at 10 kg/cm$^2$ at 1,000 rpm for 5 minutes and then filtered through a 80 mesh stainless steel screen. Agglomerates retained on the screen were thoroughly washed with water and weighed. Percents of the agglomerates relative to the charged quantity of the monomer was calculated and graded according to the above schedule.
[3]The polymer film formed on the glass plate was soaked in water and the whitening to the film was observed visually.
Very Good: No whitening at all over 1 hour.
Good: Seightly whitened after 1 hour.
Fair: Whitened between 10-30 minutes.
Bad: Whitened immediately.

TABLE 6

| Surfactant combination | | | | Emulsion Stability Polymerization | Mechanical | Polymer Film Water Resistance Dried at R. T. | Dried at R. T. and cured at 110° C. |
|---|---|---|---|---|---|---|---|
| I-1 | (80%) | Na dodecylbenzene-sulfonate | (20%) | Very good | Very good | Very good | Very good |
| II-1 | (20%) | Nonylphenol/EO 50 adduct | (80%) | " | " | Good | " |
| III-1 | (20%) | Nonylphenol/EO 50 adduct | (80%) | " | " | " | " |
| IV-1 | (20%) | Nonylphenol/EO 50 adduct | (80%) | " | Good | Fair | Good |
| V-1 | (20%) | Nonylphenol/EO 50 adduct | (80%) | " | " | Good | " |

TABLE 6-continued

| Surfactant combination | | | | Emulsion Stability | | Polymer Film Water Resistance | |
| --- | --- | --- | --- | --- | --- | --- | --- |
| | | | | Polymerization | Mechanical | Dried at R. T. | Dried at R. T. and cured at 110° C. |
| I-1 | (70%) | I-2 | (30%) | " | " | " | Very good |
| V-1 | (70%) | V-2 | (30%) | Good | Very good | Very good | " |
| Nonylphenol/ EO 50 adduct | (80%) | Na dodecylbenzene-sulfonate | (20%) | Very good | Fair | Bad | Fair |

What is claimed is:

1. A compound of the formula:

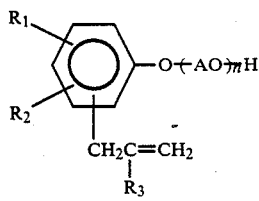

wherein
$R_1$ is alkyl, alkenyl or aralkyl of 4-18 carbon atoms,
$R_2$ is hydrogen or the same as $R_1$,
$R_3$ is hydrogen or methyl,
A is alkylene of 2-4 carbon atoms, and
n is 1-200, and
the moiety $(AO)_n$ contains an amount of oxyethylene groups effective to render the moiety hydrophilic, and the sulfate ester, phosphate ester, sulfosuccinate half ester or sulfosuccinate diester thereof and the base acid addition salt of one of said esters.

2. A sulfate ester according to claim 1, of the formula:

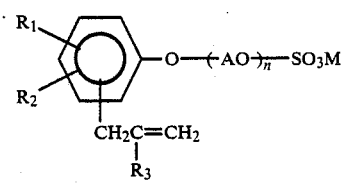

wherein M is hydrogen, alkali metal, NH₄ or lower alkanolamine, and other symbols are as defined.

3. A phosphate ester according to claim 1, of the formula:

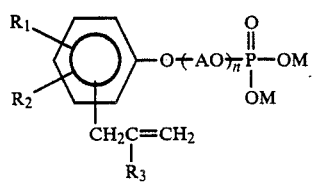

or

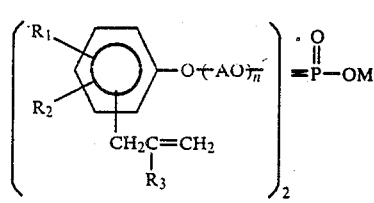

wherein M is hydrogen, alkali metal, NH₄ or lower alkanolamine, and other symbols are as defined.

4. A sulfosuccinate half-ester according to claim 1, of the formula:

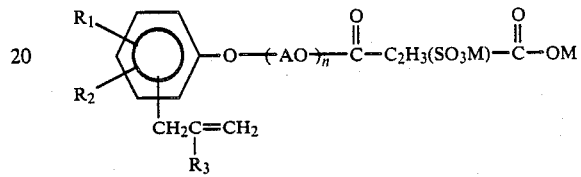

wherein M is hydrogen, alkali metal, NH₄ or lower alkanolamine, and other symbols are as defined.

5. A sulfosuccinate diester according to claim 1, of the formula:

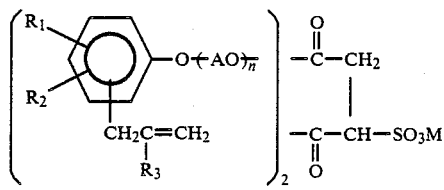

wherein M is hydrogen, alkali metal, NH₄ or lower alkanolamine, and other symbols are as defined.

6. The compound according to claim 1, wherein n is 2-100.

7. The compound according to claim 2, wherein n is 2-100.

8. The compound according to claim 3, wherein n is 2-100.

9. The compound according to claim 4, wherein n is 2-100.

10. The compound according to claim 5, wherein n is 2-100.

11. A compound of claim 1 which is a sulfate ester, phosphate ester or sulfosuccinate half- or diester or base addition salt thereof.

12. A compound of claim 1, wherein n is 4-85; $R_1$ is octyl, di-sec-butyl, nonyl, dinonyl or distyryl; $R_2$ is hydrogen; $-(AO)-$ is ethyleneoxy, propyleneoxy (block), or ethyleneoxy, propyleneoxy, butyleneoxy (random).

13. An aqueous polymer emulsion produced by the aqueous emulsion polymerization of an ethylenically unsaturated monomer in the presence of a compound of claim 1.

14. An emulsion according to claim 13, wherein the monomer is vinyl acetate or ethyl acrylate.

* * * * *